(12) United States Patent
Jones

(10) Patent No.: US 10,222,356 B2
(45) Date of Patent: *Mar. 5, 2019

(54) SEQUENTIAL OXIDATION-REDUCTION REACTOR FOR POST COLUMN REACTION GC/FID SYSTEM

(71) Applicant: Activated Research Company, LLC, Eden Prairie, MN (US)

(72) Inventor: Andrew Jones, Minneapolis, MN (US)

(73) Assignee: Activated Research Company, LLC, Eden Prairie, MN (US)

( * ) Notice: Subject to any disclaimer, the term of this patent is extended or adjusted under 35 U.S.C. 154(b) by 278 days.

This patent is subject to a terminal disclaimer.

(21) Appl. No.: 15/002,070

(22) Filed: Jan. 20, 2016

(65) Prior Publication Data

US 2016/0274072 A1 Sep. 22, 2016

Related U.S. Application Data

(60) Provisional application No. 62/136,122, filed on Mar. 20, 2015, provisional application No. 62/258,091, filed on Nov. 20, 2015.

(51) Int. Cl.
*G01N 30/46* (2006.01)
*G01N 30/68* (2006.01)
(Continued)

(52) U.S. Cl.
CPC ............ *G01N 30/68* (2013.01); *G01N 30/84* (2013.01); *B29L 2031/752* (2013.01); *B33Y 80/00* (2014.12); *G01N 2030/8435* (2013.01)

(58) Field of Classification Search
CPC ........ G01N 30/46; G01N 30/68; G01N 30/64; G01N 30/62; G01N 30/84
(Continued)

(56) References Cited

U.S. PATENT DOCUMENTS

| 7,141,207 B2 | 11/2006 | Jandeska, Jr. et al. |
| 2013/0102693 A1 | 4/2013 | Kibby et al. |
| 2013/0210936 A1 | 8/2013 | Zhou et al. |

FOREIGN PATENT DOCUMENTS

| EP | 1 061 365 A1 * | 12/2000 | ............. G01N 30/46 |
| JP | 3092873 | 9/2000 | |

OTHER PUBLICATIONS

Vincenza Dragone, et al., "3D-Printed Devices for Continuous-flow Organic Chemistry", School of Chemistry, University of Glasgow, Beilstein J. Org. Chem. May 16, 2013, 9, pp. 951-959.
(Continued)

*Primary Examiner* — Christine T Mui
(74) *Attorney, Agent, or Firm* — E. Joseph Gess; Melissa M. Hayworth

(57) ABSTRACT

Provided is a system comprising a conduit from a gas chromatograph column to a single reactor comprising a Fe, Co, Pt, Ni, Rh, Pd and/or Ru catalyst(s), with hydrogen and oxygen feed conduits for providing hydrogen and oxygen to the reactor, and a conduit from the reactor to an FID detector. This allows one to practice a method for the detection and quantification of organic molecules from a gas chromatograph which comprises passing the effluent from a gas chromatograph column to a reactor comprising a Fe, Co, Pt, Ni, Rh, Pd and/or Ru catalyst; adding hydrogen and air/oxygen to the reactor; reacting the effluent from the gas chromatograph column in the reactor to sequentially oxidize then reduce all organic containing molecules to $CH_4$ by heating to an elevated temperature, and passing the reactor effluent to an FID.

11 Claims, 4 Drawing Sheets

(51) Int. Cl.
*G01N 30/84* (2006.01)
*B33Y 80/00* (2015.01)
*B29L 31/00* (2006.01)

(58) Field of Classification Search
USPC .................. 73/23.41, 23.42, 23.35; 422/89; 436/141, 159
See application file for complete search history.

(56) References Cited

OTHER PUBLICATIONS

Written Opinion of the International Searching Authority for corresponding Patent Application No. PCT/US2016/023161, dated Jun. 27, 2016.
A. Jones et al. "From Laboratory Research to Disruptive Commercializatio" MN ACS Meeting Presentation, Feb. 16, 2016, [retrieved form the Internet on May 30, 2016] <URL:http//www.activatedresearch.com/Public_documents/PA_ACS_PPT_1551.pdf>; entire document.
"3D-Printed Reactor Speeds Chemical Analysis". Proto Labs. Online Article. Oct. 15, 2015 [retrieved form the Internt on May 31, 2016]. <URL:https://www. protolabs.com/resources/case-studies/activated-research-company/>; entire document.
International Search Report for corresponding Patent Application No. PCT/US2016/023161, dated Jun. 27, 2016.
T. Watanabe et al. "Development of a precise method for the quantitative analysis of hydrocarbons using post-column reaction capillary gas chromatography with flame ionization detection." Chromatography, vol. 27 (Mar. 8, 2006), pp. 49-55.
S. Maduskar et al. "Quantitative carbon detector (QCD) for calibration-free, high resolution characterization of complex mixtures." Royal Society of Chemistry, (Nov. 2014) Lab on a Chip.

\* cited by examiner

SEQUENTIAL OXIDATION-REDUCTION REACTOR FOR POST COLUMN REACTION GC/FID SYSTEM

CROSS REFERENCE TO RELATED APPLICATIONS

The present application claims priority to U.S. Provisional Application No. 62/136,122 filed Mar. 20, 2015 and U.S. Provisional Application No. 62/258,091 filed Nov. 20, 2015, with the contents of each application incorporated herein by reference in their entirety.

BACKGROUND OF THE INVENTION

Gas chromatography (GC) is a technique for separating molecules to allow for the detection and quantification of isolated species. The flame ionization detector (FID) is the most commonly used GC detector because of its ease of operation, robustness and high sensitivity to most carbon-containing molecules. The separation, detection and quantification of carbon-containing molecules, is efficiently and accurately done with gas chromatograph and flame ionization detection. However, current implementations of GC with FID (GC/FID) require the calibration of the response of the FID to particular molecules, which depends on the molecular structure, composition and concentration. Moreover, certain carbon-containing molecules have low or negligible response in the FID, including, for example, carbon monoxide (CO), carbon dioxide ($CO_2$), carbon disulfide ($CS_2$), carbonyl sulfide (COS), hydrogen cyanide (HCN), formamide ($CH_3NO$), formaldehyde ($CH_2O$) and formic acid ($CH_2O_2$).

The conversion of carbon-containing molecules at the exit of GC columns into methane ($CH_4$) prior to their introduction into the FID increases the detection sensitivity to carbon-containing molecules and leads to similar per carbon responses of the FID regardless of the chemical origin of the methane. In one such embodiment, the GC column effluent is combusted in a palladium (Pd) containing reactor containing an oxygen or air co-feed, the resulting carbon monoxide (CO) and carbon dioxide ($CO_2$) products are subsequently converted to methane in a reduction chamber containing nickel (Ni) and a hydrogen gas ($H_2$) co-feed.

Prior art of interest includes a system used for testing GC machines by use of standards of known concentration and composition, involving two separate reaction vessels separated with a 4-port valve and tubing (T. Watanabe et al. "Development of a precise method for the quantitative analysis of hydrocarbons using post-column reaction capillary gas chromatography with flame ionization detection." Chromatography, vol. 27 (Mar. 8, 2006), pp. 49-55.). This combustion reaction chamber utilized a commercially available palladium-asbestos catalyst packed into a stainless steel tube containing quartz wool. The reduction catalyst described by this system was a commercially available nickel catalyst for a methanizer packed into a stainless steel tube containing quartz wool. This system also included separate temperature controls and heating elements for the combustion and reduction chambers.

Other prior art of interest includes a system comprising multiple couplings, and $H_2$ and air inlets outside of the heated block included in the system (S. Maduskar et al. "Quantitative carbon detector (QCD) for calibration-free, high resolution characterization of complex mixtures." Royal Society of Chemistry, (November 2014) *Lab on a Chip*.). The system used a commercially available catalyst consisting of 10% Pd/alumina for the combustion chamber, and a commercially available nickel on diatomaceous earth catalyst for the reduction chamber.

SUMMARY

The present invention pertains to a device for the conversion of organic molecules into methane designed for the integration with GC/FID systems. It has been found that a small reactor with small internal channels minimizes changes in peak retention time in the GC and eliminates appreciable peak broadening and tailing. The small reactor allows for rapid heating and cooling, and the welded design eliminates fittings that can cause leaks. These innovations have been found to be made possible by the improvement of three dimensional metal printing technologies, which allow for the production of complex internal channel geometries and reactor design, far more complex and compact than those afforded by traditional machining processes. These innovations represent a significant improvement in the performance of methane generation for GC/FID applications in a small device with low costs that can be integrated seamlessly with existing GC technology.

In one embodiment, the present invention reduces the two separate reaction vessels setup to a single reactor block with embedded reaction channels that significantly improve heat transfer and flow dynamics to improve performance and mitigate peak broadening and tailing of the effluent as detected by the FID. The small size of the device allows it to be integrated into a number of existing gas chromatography models. The design and catalyst selection allow for the reaction and detection of molecules by the FID that were previously impossible to detect or marginally detectable.

Among other factors, the present invention pertains to capillary components that improve the performance and flow dynamics of a device for the conversion of organic molecules into methane designed for the integration with GC/FID systems. Furthermore, the flow tubes and/or the reactor body are optionally coated with a silicon layer to improve inertness and minimize unfavorable reactions and interactions of molecules with the stainless steel tubes and reactor body. The innovative use of these components and their novel implementation in this type of reactor lead to the more seamless integration of this device into the majority of GCs, namely those with capillary components, and enhanced chromatographic performance.

DETAILED DESCRIPTION

Figure 1:
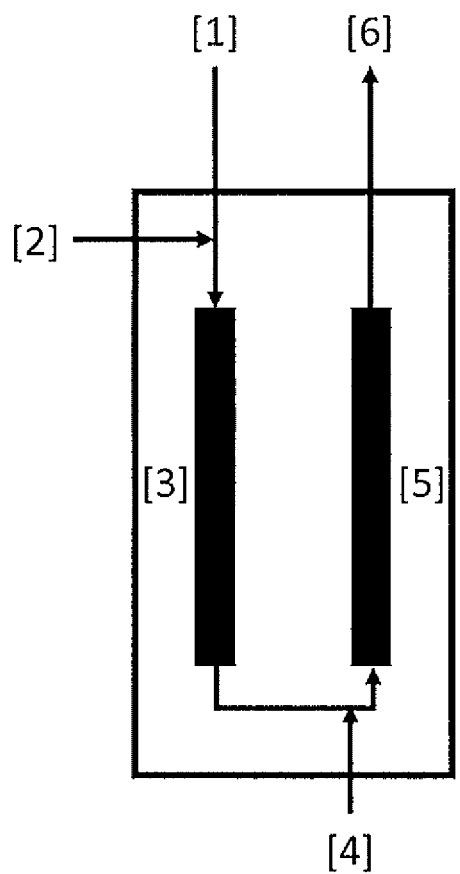
FIG. 1 is a schematic of an embodiment of the present system.

Provided by the present invention is a system comprising a conduit from a gas chromatograph column to a solid metal component comprising catalysts containing platinum (Pt), nickel (Ni), palladium (Pd), cobalt (Co), iron (Fe), rhodium (Rh) and/or ruthenium (Ru). The catalysts have been selected to provide complete conversion of any carbon-containing species to carbon dioxide and then subsequently to methane, but also to limit the inhibition of reaction rates due to the presence of heteroatom species such as S, Cl, F, and N. The selection of catalysts also affects the residence times required and the resulting peak broadening potential that can be detrimental to optimum GC performance.

The component, or reactor, contains small channels, between 0.025 to 0.38 cm internal diameter (id), for the oxidation and reduction zones and for gas connections. The size and geometry of the channels have been selected to provide adequate volume for catalysts and gas flows to minimize pressure drop, and to promote flow dynamics that enable high conversions while minimizing axial dispersion and back mixing. Large pressure drops lead to difficult flow control, incompatibilities with gas chromatographs and other detrimental effects to analysis. Flow dynamics are important to ensure complete conversion, but also to minimize mixing in the axial flow directions that give rise to poor separations of the GC column effluents and poor signal shape. By using the inventive small channel reactor, one can detect and quantify organic molecules without the necessity of calibration.

Overall, the present system includes several improvements on the prior art. It eliminates several valves and fittings, thereby reducing dead-volume within the reactor and reducing the possibility of peak-broadening of compounds detected by the FID. The system is completely enclosed in a single block allowing for even conduction of heat by a heating element and optimal flow dynamics to and within the reactor. The reduced size of the system over prior examples allows it to be easily integrated into a variety of commercially available gas chromatography machines. The catalysts selected for the reduction chamber and the oxidation chamber of the system ensure near-complete conversion of the carbon containing compounds to methane.

The system is also an improvement on the prior art in its ability to detect carbon containing compounds from a wide variety of sources, not only pure hydrocarbons, but also compounds with a wide variety of heteroatoms (oxygen (O), sulfur (S), chlorine (Cl), fluorine (F), nitrogen (N) and more).

Another improvement of the present system is the use of capillary tubes (defined as a tube with an inner diameter less than 0.6 mm) for the inflow and outflow portions of the device to further reduce dead volume. The capillary allows the system to be connected to a variety of gas chromatographs on the market without the need for additional, unnecessary fittings and adapters. The use of capillary tubes also increases the resolution of the FID by reducing the volume of the inflow and outflow tubes, thereby reducing the dispersion of the analyte through the system. The capillary tubes are directly attached to the reactor without the use of fittings; fittings are cumbersome, expensive, prone to leaks, and can lead to undesirable flow characteristic (pressure drops, axial dispersion, dead volume etc.). Furthermore, the system is optionally coated in a silicon layer to decrease interactions of species with the metal surface and improve separation and detector response.

The current invention achieves the near complete reactions to methane of a wide variety of carbon-based molecules that contain heteroatoms such as O, S, Si, C, F, and N, which have not been demonstrated previously. The results demonstrate the applicability of the current system for the detection of nearly all molecules containing carbon atoms without the need for calibration in GC/FID systems.

In one embodiment, the system comprises hydrogen and air or oxygen feed conduits to the reactor, a conduit from the reactor to an FID detector and a conduit from the reactor to a GC column. The conduits are physically mated to the reactor body. In one embodiment the conduits are laser sintered to the component. The elimination of fittings due to the solid component design and the physical mating of the conduits improves flow dynamics by nearly eliminating mixing areas and dead volume in the reactor, and improves the overall performance of the device.

The catalytic conversion to methane is accomplished by heating the reactor to an elevated temperature in the presence of a catalyst, and air and hydrogen gases. In one such embodiment, the elevated temperature for the reaction is in the range of 425-475° C. The temperature selected must be high enough to ensure kinetics for the combustion of a wide range of carbon-containing compounds, but low enough that methane production is favored thermodynamically.

The catalysts are supported on substrates that may include silica, alumina, silica-alumina or titania. The substrate-catalyst interactions influence the dispersion of the metal catalyst particles, which can lead to reactivity differences. The appropriate support structure and composition of the catalysts have been chosen to control the density of the catalyst on the support and in the reactor for optimal reaction kinetics, heat transfer and flow dynamics.

The ideal reactor has a length of 2.5-7.6 cm, a width of 1.25-5 cm and a height 0.25-2.5 cm. The small size has been chosen to allow for rapid and efficient heat transfer from commercially available resistive heater element cartridges. The size is also large enough to have an appropriate thermal mass to prevent temperature fluctuations, in part, from the transient reactions during GC operation. The size is also appropriate for fully containing small internal channels and the required linkages with external conduits.

The reactor is constructed with three dimensional laser sintering (3D printing) to allow for the construction of small and complex internal geometries. Small channels and seamless construction are essential for minimizing dead volumes, rough edges, and corners that can lead to poor separation performance. Machining processes are unable to create an intricate device such as the claimed invention without a loss of complexity and the formation of dead volumes where gases can become trapped and are not subject to convection of gas flows through the device.

The internal dimensions of the conduits attached to the component are adjusted to fit different systems to which the Invention may be added. Capillary tube columns (0.1-0.53 mm internal diameter) are the most common separation devices used in GC, but larger packed columns (0.75-2.1 mm) exist. In one embodiment metal tubes with internal diameters between 0.25-0.9 mm, and external diameters between 1.5-3.2 mm are mated directly with the component. In another embodiment tubes with outer diameters between 0.2-0.8 mm and inner diameters between 0.1-0.53 mm are used as conduits that connect the component to capillary tube columns and to flame ionization detectors. These capillary tubes are welded to the reactor body via tubular strain reliefs that provide structural support and minimize the fracture of sensitized capillary tubes at weld points. The strain reliefs are ideally stainless steel tubes with an outer diameter between 3-4.2 cm and an inner diameter between 0.5-1.3 mm. The length of the strain reliefs are ideally between 2.5 and 21 cm. All components are stainless steel and solderless welds are used to eliminate any incompatibilities between different metals. The inner diameters and lengths of the metal capillary tubes are chosen to minimize axial dispersion, dead volume and pressure drop that can adversely affect GC separation performance. The inner diameter of the metal capillary outlet to the reactor block is larger than the outlet to minimize pressure drop throughout the reactor due to the addition of air and hydrogen flows at different points in the flow path. In addition, the outer diameters of the capillary tubes are chosen to conform to the inlet requirements of the FID and the capillary columns of the GC. This allows for the minimization of fittings that are detrimental to GC performance and integration.

In one embodiment the conduits and reactor body are coated with a silicon layer in a commercial process that yields a homogeneous, inert, glass-like layer over the stainless steel. This layer minimizes undesirable reactions and interactions of certain components in GC effluents with the internal walls of the Invention. The silicon layer is ideally approximately 100 nm thick and imbues a pinkish glow only at certain thicknesses.

One embodiment of the present system is depicted schematically in FIG. 1. In the figure, conduits are mated directly to the component, which contains internal channels of varying geometries to control flow dynamics and reactions. The gas flow from the exit of the GC column is transferred from a conduit [1] and combined with an $O_2$ mixture (e.g., air between 0.5-10 $cm^3$ $min^{-1}$ but ideally 2.5 $cm^3$ $min^{-1}$) from another conduit [2]. This mixture flows through channels packed with Ni, Pt, Fe and/or Pd catalysts [3]. The effluent from [3] is then mixed with $H_2$ (10-60 $cm^3$ $min^{-1}$ but ideally 35 $cm^3$ $min^{-1}$) [4], and subsequently flows through channels packed with Ni, Co, Fe, Rh and/or Ru catalysts within the device [5]. The volume of the internal channels is 0.1-4 $cm^3$, but preferably about 1 $cm^3$. Internal geometries and packing's prevent the loss of catalyst particles. The effluent from the component is connected to an FID through another conduit [6]. It has been found that the size of the reactor channels allows for near complete carbon conversion to $CH_4$ with >99.9% carbon selectivity with minimal impact on GC separation performance. The device is entirely contained within a metal block heated between 300-550° C. by a resistive heater with a temperature measuring device (e.g., a thermocouple or resistive thermal device).

Figure 2:
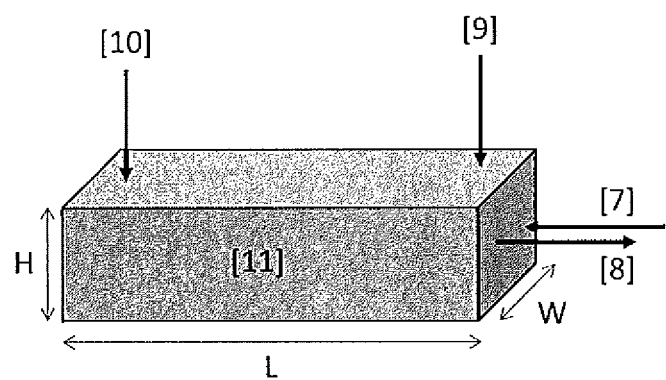
FIG. 2 is a diagram of one embodiment of the present invention.

The body of the device [11] is depicted schematically in FIG. 2. The device has a length, L, 2.5-7.6 cm, a width, W, 1.25-5 cm and a height, H, 0.25-2.5 cm. The device is ideally 5 cm×2.5 cm×1.25 cm in size. This size provides a balance of fast heat transfer and appropriate thermal mass, while containing the appropriate channels and heater cavities. Metal tubes are mated to the reactor to provide conduits for gas flows. The mating can be performed using laser welding without solder to provide a gas-tight seal that withstands high-temperature treatments in air. GC effluents are transferred to the component through a conduit [7], and the reacted gases are transferred to the FID via another conduit [8]. Air or oxygen, and $H_2$ are added to the reactor via conduits [9] and [10], respectively.

Figure 3:
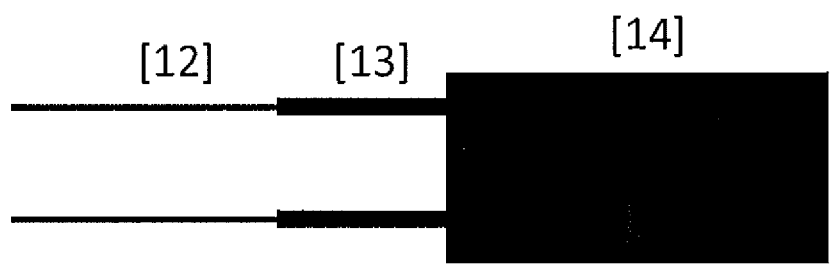
FIG. 3 shows the capillary connections to the reactor body.
Figure 4:
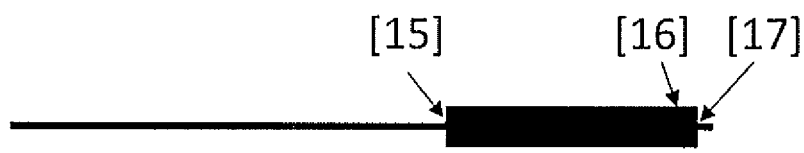
FIG. 4 shows a capillary mating to its sheath.

Small inflow and outflow tubes (capillary) are provided in one embodiment of the device and are depicted schematically in FIG. 3. In the Invention, gas flows are transferred from the GC column and the FID to the reactor via capillary tubes [12] that are supported by strain reliefs [13] mated directly to the reactor body [14]. A strain relief and capillary attachment is detailed in FIG. 4, whereby the capillary tube is welded to the end of the strain relief [17] and the strain relief is welded directly to the body of the reactor around the outside of the strain relief [16]. This process creates a leak-tight seal that minimizes the strain on the capillary tube at the critical weld joint. The welding of the capillary tube to the inside of the strain relief at the back-end [17] and not the front-end [15] is necessary because the welding weakens the capillary tube and would easily break off of the front-end [15] during normal use and installation. The capillary tube protrudes slightly out of the strain relief at the back-end [17] to allow for welding and prevent tube collapse. The strain relief also allows for heat conduction to the capillary tube to minimize cold spots along the tube as it carries gases to the GC oven through an unheated zone. The inside edge of the strain relief [15] is chamfered at no less than a 15° angle to minimize scoring of the capillary tube and lead to a higher safe bend radius.

The device is constructed using three-dimensional metal printing technology, which allows for the unparalleled control of internal geometries. Alternatives to three-dimensional printing for reactor construction, such as machining, are not able to create the small complex geometries required in the current Invention. Three-dimensional metal printing of the device is accomplished with the appropriate design of the reactor in modeling software and the subsequent conversion of these files to instructions for the selective laser sintering printing systems using commercially available hardware and software. Selective laser sintering printers are available commercially from, for example, 3D Systems. The printer constructs the body of the reactor, including the complex internal geometry, layer-by-layer to completion. The catalyst is packed into the reactor after or during the printing process using mechanical force or injected as a slurry. The small size of the device increases the thermal response, and allows for easy placement and integration within existing GC hardware. The seamless construction assists in maintaining a uniform temperature distribution, and the internal reactor volume and geometries are selected to eliminate axial dispersion and dead volume to ensure a better GC separation and detection.

It has been found that this single reactor system improves upon the prior two-reactor scheme for generating $CH_4$ because of the solid one-piece design that eliminates leaks and optimizes heat transfer, and the small form factor allows for easy placement in existing GC equipment without modification. The present single reactor also minimizes the detrimental effects of peak broadening and tailing observed in other systems. In addition, the completely contained reactor system eliminates the need for complicated piping configurations required in prior systems, reducing costs substantially. The enclosed device eliminates the handling of catalysts, which contain known health hazards, and essentially eliminates their unintended release. The present system reliably converts all carbon-containing compounds regardless of heteroatom identity and quantity, including S, Cl, F, N, O and more. This improves upon previous reactors that are poisoned by small amounts of heteroatoms such as sulfur.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A system comprising:
 a single metal block which has been constructed using three dimensional printing, having channels of a size of 0.025 to 0.38 cm internal diameter, the channels containing catalysts including Ni, Pt, Pd, Co, Fe, Rh and/or Ru;

a conduit from a gas chromatograph to the block, with the conduit feeding to the channels in the block containing the catalysts;

a hydrogen conduit for providing hydrogen to the block;

an air or pure oxygen conduit for providing oxygen to the block; and a conduit from the block to a flame ionization detector (FID).

2. The system of claim 1, wherein the conduits are welded to the single metal block.

3. The system of claim 1, wherein the catalysts are supported on silica, alumina, silica-alumina, or titania.

4. The system of claim 1, wherein the single metal block has a length 2.5-7.6 cm, a width 1.25-5 cm and a height 0.25-2.5 cm.

5. The system of claim 1, further comprising capillary tubes as conduits.

6. The system of claim 5, wherein the capillary tubes have inner diameters between 0.1-0.53 mm.

7. The system of claim 5, wherein the capillary tubes are surrounded by a support.

8. The system of claim 7, wherein the support is mated to the capillary tubes.

9. The system of claim 7, wherein the support is mated to the system of claim 1.

10. The system of claim 1, further comprising that the block and/or conduits are coated with silicon.

11. The system of claim 5, wherein the capillary tubes have been mated to a support by laser welding.

* * * * *